(12) United States Patent
Münchmeyer et al.

(10) Patent No.: US 9,404,889 B2
(45) Date of Patent: Aug. 2, 2016

(54) METHOD AND DEVICE FOR DETECTION AND IDENTIFICATION OF GASES

(75) Inventors: Wolf Münchmeyer, Ehra-Lessien (DE); Bert Ungethüm, Schwerin (DE); Andreas Walte, Schwerin (DE)

(73) Assignee: Airsense Analytics GmbH, Schwerin (DE)

( * ) Notice: Subject to any disclaimer, the term of this patent is extended or adjusted under 35 U.S.C. 154(b) by 194 days.

(21) Appl. No.: 12/863,553

(22) PCT Filed: Jan. 12, 2009

(86) PCT No.: PCT/DE2009/000023
§ 371 (c)(1),
(2), (4) Date: Aug. 30, 2010

(87) PCT Pub. No.: WO2009/089818
PCT Pub. Date: Jul. 23, 2009

(65) Prior Publication Data
US 2010/0314548 A1    Dec. 16, 2010

(30) Foreign Application Priority Data
Jan. 19, 2008    (DE) .......................... 10 2008 005 281

(51) Int. Cl.
*G01N 27/64* (2006.01)
*G01N 27/62* (2006.01)
*H01J 49/00* (2006.01)

(52) U.S. Cl.
CPC ............ *G01N 27/624* (2013.01); *G01N 27/622* (2013.01); *H01J 49/0027* (2013.01); *H01J 49/0031* (2013.01)

(58) Field of Classification Search
CPC ... G01N 27/624; G01N 27/62; G01N 27/622; H01J 49/0027; H01J 49/0031; H01J 49/0036; H01J 49/40; H01J 49/403

USPC .................................................. 250/281–300
See application file for complete search history.

(56) References Cited

U.S. PATENT DOCUMENTS

| 3,621,240 A | 11/1971 | Cohen et al. |
| 4,445,038 A | 4/1984 | Spangler et al. |

(Continued)

FOREIGN PATENT DOCUMENTS

| CN | 1759312 A | 4/2006 |
| DE | 4134212 A1 | 4/1993 |

(Continued)

OTHER PUBLICATIONS

International Search Report Dated Jun. 12, 2009.

(Continued)

*Primary Examiner* — Michael Logie
(74) *Attorney, Agent, or Firm* — Norris McLaughlin & Marcus, P.A.

(57) ABSTRACT

Methods and devices identify gases and allow immediate and simultaneous detection of the chemical compounds to be tested. The methods and devices use a function of the electric field strength, for identification the material-specific mobility and simultaneously the change in this mobility, which is achieved in that due to the resulting electric field, each ionized molecule has a drift velocity which is partially increased or decreased, wherein the resulting electric field is a DC field, on which an asymmetric AC field is superimposed. The methods and devices for the detection and identification of gases are used to identify and detect chemical compounds, such as, explosive and/or unhealthy substances or compounds, which may be detected in very small concentrations.

18 Claims, 4 Drawing Sheets

(56) References Cited

U.S. PATENT DOCUMENTS

Figure 1:
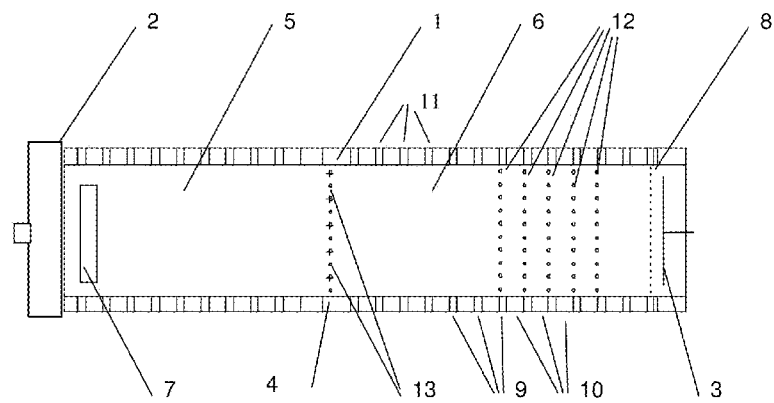

| | | | |
|---|---|---|---|
| 5,420,424 A | 5/1995 | Carnahan et al. | |
| 6,495,823 B1 | 12/2002 | Miller et al. | |
| 6,504,149 B2 | 1/2003 | Guevremont et al. | |
| 6,509,562 B1* | 1/2003 | Yang et al. | 250/287 |
| 7,696,474 B2* | 4/2010 | Wu et al. | 250/281 |
| 7,812,305 B2* | 10/2010 | Miller et al. | 250/287 |
| 7,829,849 B2* | 11/2010 | Giles | 250/290 |
| 7,902,498 B2* | 3/2011 | Miller et al. | 250/282 |
| 7,977,627 B2* | 7/2011 | Atkinson et al. | 250/287 |
| 2004/0079879 A1* | 4/2004 | Ross et al. | 250/287 |
| 2005/0082472 A1* | 4/2005 | Dahms et al. | 250/287 |
| 2005/0178964 A1* | 8/2005 | Guevremont et al. | 250/294 |
| 2006/0038121 A1* | 2/2006 | Guevremont | 250/287 |
| 2006/0097156 A1* | 5/2006 | Guevremont | 250/290 |
| 2006/0132379 A1 | 6/2006 | Peterson | |
| 2007/0023635 A1* | 2/2007 | Bateman et al. | 250/282 |
| 2007/0023638 A1* | 2/2007 | Bateman et al. | 250/287 |
| 2008/0210861 A1* | 9/2008 | Wu et al. | 250/287 |
| 2009/0200459 A1* | 8/2009 | Zimmer | 250/282 |
| 2009/0309019 A1* | 12/2009 | Atkinson et al. | 250/282 |
| 2011/0036977 A1* | 2/2011 | Denton et al. | 250/283 |
| 2011/0095175 A1* | 4/2011 | Bateman | 250/282 |
| 2011/0260053 A1 | 10/2011 | Atkinson et al. | |

FOREIGN PATENT DOCUMENTS

| | | |
|---|---|---|
| DE | 19513459 A1 | 1/1996 |
| DE | 19515270 A1 | 11/1996 |
| JP | 2007534126 A | 11/2007 |
| JP | 2009-522750 A | 6/2009 |
| WO | 03/081224 A1 | 10/2003 |
| WO | 2005/067582 A2 | 7/2005 |
| WO | 2005/106450 A1 | 11/2005 |
| WO | 2006/114580 A | 11/2006 |
| WO | 2007/080376 A | 7/2007 |
| WO | 2007/136373 A1 | 11/2007 |

OTHER PUBLICATIONS

Eiceman, G.A., "Ion Mobility Spectrometry", Second Edition, 2005, pp. 246-249 and 252-257, CRC Press, Boca Raton, Florida.

* cited by examiner

METHOD AND DEVICE FOR DETECTION AND IDENTIFICATION OF GASES

This application is a 371 application of PCT/DE2009/000023 filed Jan. 12, 2009, which claims priority to the German application 102008005281.7 filed Jan. 19, 2008.

The invention relates to a method for identification of gases and to a corresponding device adapted for identification of gas.

Such methods and corresponding devices for the detection and identification of gases are used to detect and identify chemical substances or compounds, in particular explosive and/or unhealthy substances or compounds to be detected in very small concentrations.

The detection of explosive and/or toxic chemical compounds requires measurement techniques with detection limits in the ppt to ppb range. Spectrometers are therefore frequently used for detection and identification of these chemical compounds. The use of ion mobility spectrometers (IMS), also referred to as plasma chromatographs, is preferred because they do not require, unlike other spectrometers, for example a mass spectrometer, a vacuum pump for producing a vacuum for detecting the chemical substances or compounds. IMS are therefore compact and inexpensive compared to other spectrometers.

IMS can be used in a large number of applications, ranging from the medical field, for example for testing the air exhaled by patients, for monitoring production, for example for quality control in a coffee roasting facility, to the military field, for example for detecting chemical warfare agents. General review of IMS and its applications can be found, for example, in G. A. Eiceman and Z. Karpas "Ion Mobility Spectrometry" (2nd. Edition, CRC, Boca Raton, 2005).

The structure and operation of the IMS has been described in numerous publications. For example, U.S. Pat. No. 3,621,240 describes a classical time-of-flight IMS which takes advantage of the different mobility of ions at atmospheric pressure. The target compounds are continuously ionized in an ion source either by radioactive radiation, photo-ionization or corona discharge. Frequently, radioactive sources are used which directly ionize the air molecules. These ionized air molecules react further and form, together with water molecules, so-called reactant ions. These reactant ions react by proton transfer, electron transfer or proton abstraction reactions with the compounds of interest, forming the so-called product ions. The product ions are introduced into a drift tube within a very short time span of about 200 µs as with the help of an electric grid, which has an electric field and which accelerates the ions in a drift gas, typically filtered air at atmospheric pressure. By changing the polarity of the electric field of the drift section, positive ions can be detected in a positive operating mode and negative ions can be detected in a negative operating mode. The introduced product ions are continuously accelerated by the electric field and continuously decelerated through collision with the neutral molecules in the drift gas. All ions having the same charge experience the same pulling force in the electric field. Because the product ions have different parameters and shapes, the product ions also have different drift velocities. At the end of the drift tube, the product ions with these different drift velocities impact on a detector. From the different times of flight of the product ions through the drift tube, which are typically in a range of 5 to 30 milliseconds, conclusions can be drawn about the tested chemical compounds.

The start pulse for measuring the drift velocity in the classical time-of-flight IMS is provided by the switching process of the electric grid, which only lets a portion of the ions enter the drift space. Collisions with the molecules of the ambient air cause diffuse broadening of the introduced ions. The signal measured at the detector has therefore the shape of a Gaussian bell curve. The drift velocity can be determined from the measured time-of-flight or from the drift time at the maximum of the bell curve and the known length of the drift section, whereby a resulting spectrum can be used for identifying the chemical substances or compounds.

The time-of-flight of the product ions through the drift tube is proportional to the drift velocity with which the product ions impact on the detector. The drift velocity, due to the acceleration in the electric field and the deceleration through collisions between the ions and the neutral molecules in the drift gas, depends in turn on the ion mass or ion size and the ion shape.

The drift velocity of the product ions $v_d$ depends at a small field strength E, e.g., E=200 V/cm, linearly on the field strength. At these small field strengths, the mobility K of the product ions is then independent of the field strength and can be expressed as follows:

$$K = v_d/E.$$

Because the drift velocity of the ions depends also on the temperature and pressure in the drift tube, the mobilities of the product ions are always normalized for identification and detection of the chemical compounds to standard conditions, meaning a standard temperature $T_0=273°$ K and a standard pressure $p_0=1013$ hPa. The reduced or normalized mobilities of the product ions can then be expressed as follows:

$$K_0 = K \cdot (T_0/T) \cdot (p/p_0) = K \cdot (273° \text{ K}/T) \cdot (p/1013 \text{ hPa}).$$

Using the classical time-of-flight IMS has the disadvantage that only a small portion of the product ions is used for the detection and hence also for the evaluation of the tested chemical compounds. Because the start pulse of the electric grid is very short compared to the drift time of the ions, only a small portion of the product ions enters the drift tube through the grid. The larger portion of the product ions impacts on the grid when the grid is closed, and is neutralized on the grid.

As a result, the yield of the product ions reaching the drift tube and hence also the detection limit of the tested chemical substances or compounds can be increased by increasing the ion throughput in combination with a modulation of the ion beam with blocking grids. Such modulation of the ion beam is proposed, for example, in DE 19515270 C2, allowing the computation of the time-of-flight spectrum of the IMS by way of a mathematical transformation, for example with Hadamard or Fourier transformations.

Disadvantageously, only positive or negative ions can be measured with the aforedescribed IMS, requiring a change in the polarity of the separation tube, which increases the measurement time. In addition, several toxic industrial chemicals, for example benzene, cannot be measured with a radioactive source, because the product ions impact on the detector simultaneously with the reactant ions.

U.S. Pat. No. 5,420,424, U.S. Pat. No. 6,495,823 or U.S. Pat. No. 6,504,149 therefore disclose a Differential Mobility Spectrometer (DMS) or Field Asymmetric Ion Mobility Spectrometer (FAIMS-Spectrometer), which is composed of an ion source, electrodes and a detector, wherein the ions, after the ions are formed, pass through two parallel electrodes together with the neutral molecules in a constant gas flow. The electrodes can either be plan-parallel or axially symmetric. A high and a low voltage is alternatingly applied to the electrodes. The electric field acts here, unlike in the classical time-of-flight IMS, perpendicular to the flow direction of the ions. The asymmetric AC voltage is selected so that the average voltage cancels out. A description of this AC voltage for separating ions based on the different changes in the ion mobilities at high field strengths can be found, for example, in SU 966583. According to E. A. Mason and E. W. McDaniel in "Transport Properties of Ions in Gases" (Wiley, New York, 1988), the mobility is no longer independent of the field strength at very high field strengths, e.g., E>5000 V/cm.

Unlike with classical time-of-flight IMS, the ions are separated with DMS by taking advantage of the different changes in the mobilities of the ions at small and high electric field strengths. The separation of the ions is then due to the difference of the mobilities $K(E_{low})$ and $K(E_{high})$ of the ions. This difference in the mobilities $K(E_{low})$ and $K(E_{high})$ of the ions is different for different chemical compounds, so that with DMS the material-dependent properties of the mobilities of the ions as a function of the electric field strength can be used.

The drift velocity of the ions at high field strengths can be expressed as follows:

$$v_d = K(E)*E.$$

The non-constant mobility $K(E)$ can be represented by a series expansion with polynomial coefficients:

$$K(E) = K + k_1 * E^2 + k_2 * E^4 + \ldots$$

or by a function $\alpha(E)$:

$$K(E) = K*(1 + \alpha(E)).$$

The function $\alpha(E)$ describes the non-linear dependence on the electric field which is different for chemical compounds. For example, the function $\alpha(E)$ may increase with increasing field strength, may decrease with increasing field strength, or may first increase with increasing field strength and then decrease again at a higher field strength. Accordingly, chemical compounds can be grouped into three categories, depending on the dependence on the field strength. For ions of type A, the mobility of the ions increases with increasing field strength, for ions of type C, the mobility decreases with increasing field strength, whereas for ions of type B the mobility first increases with increasing field strength and then again decreases at a higher field strengths.

The decrease in the mobility of the ions with increasing field strengths, i.e., for type C, is caused by the dependence of the mobility on temperature, because the collision frequency increases at higher temperatures. The increase in the mobility with field strength, i.e., for type A, is due to the decrease in the ion size at high field strengths. A molecule ion $M^+$ to be measured is always surrounded by water molecules at atmospheric pressure, so that it is present as a water cluster $MH^+(H_2O)_n$, with two to three water molecules being typically arranged around the molecule. However, the water molecules are only weakly bound to the molecule ion, so that water molecules of some chemical compounds can be split off at very high field strengths due to the higher drift velocities, thereby reducing shape and mass, allowing these product ions to move faster through the drift gas. The water molecules from the drift gas are again deposited at lower field strengths by collision processes.

With the asymmetric AC voltage, the lower voltage of one polarity acts significantly longer on the ions than the high voltage of the other polarity. Ions without a field-dependent mobility are therefore not a deflected and reach the detector directly. Because the mobility of most compounds depends on the field strength, the oscillating ions are on average deflected, so that for example the ions of type A are deflected in the direction of the high field strengths. To detect these ions at the detector, a DC voltage or deflection voltage is superimposed on the electrodes having the AC voltage, allowing the ions to reach the detector. By gradually changing the DC voltage, also referred to as compensation voltage, only certain ions with a corresponding $\alpha(E)$-value are allowed to pass through. If this voltage is applied in form of a sawtooth voltage, a spectrum is generated where the x-axis represents not the drift time, but the compensation voltage. Unlike with the classical time-of-flight IMS, the separation is not performed based on the absolute mobility, because compounds with different mobilities that do not depend on the field strength, i.e. $K(E_{low})=K(E_{high})$, are not separated by the asymmetric AC field, because the deflection cancels out on average.

Because in DMS the ions are transported only by the gas flow, positive and negative ions reach the separation field simultaneously. By arranging two detectors with different polarity at the end, positive and negative ions can be detected simultaneously with these IMS.

With a plan-parallel structure of the electrodes, the distance between the electrodes is, for example, only 0.5 mm, so that typically approximately rectangular AC voltages of about $E_{high}=20$ kV/cm and $E_{low}=1$ kV/cm can be applied at a frequency of 1 MHz. With this structure, the compensation voltage is increased from −15 V to +10 V within several seconds.

If the field strength is varied in addition to the compensation voltage, i.e., also the $E_{high}$-value is also changed, separation of the ions can be additionally optimized, whereby the results can be summarized in a so-called dispersion plot, wherein the compensation voltage is plotted as a function of the high field strength and the intensity of the detector signal is represented in color.

When using a DMS, the measurement disadvantageously takes a long time when measuring unknown chemicals, because time-consuming changes in the compensation voltages and the AC voltage amplitudes are necessary for adjusting the dispersion plot. In addition, the resolution and therefore the separation of larger ions, for example when separating phosphor-organic compounds, is worse with DMS than with the classical time-of-flight IMS, as disclosed for example in WO 2005/106450.

For this reason, WO 2005/067582 proposes to combine at least one DMS with a classical time-of-flight IMS. In one exemplary embodiment, one DMS and one classical time-of-flight IMS are arranged in parallel behind an ion source, wherein both spectrometers operate independently of each other.

In another exemplary embodiment, one classical time-of-flight IMS or, alternatively, two mutually parallel classical time-of-flight IMS are arranged behind a DMS system, wherein the latter embodiment allows simultaneous measurement of positive and negative ions that have already exited the DMS system.

Disadvantageously, this combination of DMS and classical time-of-flight IMS is technically quite complex, because in particular in the last exemplary embodiment, two classical time-of-flight IMS drift tubes and one DMS need to be configured and combined. In addition, with this combination of DMS and classical time-of-flight IMS, the measurement time is long and an instantaneous detection of the tested chemical compounds is impossible, because the DMS as the first separation system must at least go through the compensation voltages which requires several seconds to minutes.

It is therefore an object of the invention to develop a generic method of the aforedescribed type for identifying gases and a corresponding device which has a simple structure and allows an instantaneous and simultaneous detection of the chemical compounds to be tested, and which uses for identification the material-specific mobility and also the change of this mobility as a function of the electric field strength.

This object is attained with the method disclosed herein and with the device disclosed herein. Advantageous embodiments of the method and device are also disclosed herein.

The novel method for identification of gases and the corresponding device obviate the aforementioned disadvantages of the state-of-the-art.

With the novel method for identification of gases, each ionized molecule advantageously has a drift velocity due to the resulting electric field, which is partially increased or decreased, wherein the resulting electric field is a DC voltage field on which an asymmetric AC field is superimposed. The resulting change in the drift velocity, i.e., the partially increased or decreased drift velocity, it is due to the fact that each ionized molecule performs in the resulting electric field a constant drift movement on which an oscillating movement is superimposed. If the drift velocity of an ionized molecule is partially increased or decreased, is ion-specific and depends on the material properties of the molecule. These partially increased or decreased drift velocities of the ionized molecules are used for characterizing and differentiating between these ionized molecules. The drift times of the ionized molecules along a drift space are measured and evaluated from these drift movements.

Advantageously, each ionized molecule is accelerated and decelerated several times, wherein on average, depending on the material properties of the molecule, the acceleration is greater or smaller than the deceleration. The ionized molecules can be positive and/or negative ions which are used either with different operating modes of the drift tube associated with the drift space or with two drift tubes operating with opposite polarities. The drift times are measured by first accelerating the ionized molecules with the resulting electric field until they reach a constant drift velocity. Thereafter, these molecules are additionally partially accelerated and decelerated, or several times accelerated and decelerated, wherein one average the time-of-flight of the ions is greater or smaller than the time-of-flight without an AC field. The resulting electric field is a DC voltage field, on which an asymmetric AC voltage field is superimposed. Unlike classical time-of-flight IMS, the asymmetric AC field superimposes an additional oscillatory movement on the drift movements, so that ions which cannot be separated with classical time-of-flight IMS due to their identical mobilities, are separated because they have higher mobilities at higher field strengths.

In a particularly advantageous embodiment, the resulting electric field is a DC voltage field on which a parallel AC voltage field is locally superimposed, so that the ionized molecules perform a drift movement in one direction and the oscillatory movement is superimposed in parallel thereto.

Advantageously, the DC voltage field has a small electric field strength and the asymmetric AC voltage field has a high electric field strength. The asymmetric AC voltage having temporarily very high field strengths causes an additional acceleration or deceleration of ions that have different $\alpha(E)$ dependencies. Advantageously, the amplitude of the asymmetric AC voltage is gradually changed and the resulting change of the drift times is used as an additional feature for identifying the measured chemical substance or compound.

Advantageously, for evaluating the measured drift times and for identifying the chemical compounds, these measured drift times are compared with previously determined drift times of known chemical compounds and/or the measured drift times and the known drift times of chemical substances and compounds are compared using mathematical or statistical methods, for example rule-based algorithms or artificial neural networks.

Advantageously, the drift times of the ionized molecules depend on changes of the mobilities as a function of the field strength for the science, because the science have a different trajectory through the drift space in an electric field of high electric field strength produced by the AC voltage electrodes than with an electric field having a small electric field strength. Advantageously, the drift times of ionized molecules with the same mobilities and small electric field strength are compared with the drift times of these ionized molecules after addition of the asymmetric AC voltage field with high electric field strength produced by the AC voltage electrodes, wherein these measured drift times are compared with the previously determined drift times for identifying the chemical compounds.

Advantageously, when using the novel device for identification of gases, at least one drift tube is delimited, on one hand, by an inlet system and, on the other hand, by a respective detector, wherein an opening and closing grid which divides the drift tube into a reaction space in a drift space is located in each drift tube, wherein an ion source is arranged in the reaction space and a shield grid is arranged in the drift space, and wherein the drift tube has several DC voltage electrodes and AC voltage electrodes arranged around the drift space.

Advantageously, and additional drift tube is delimited, on one hand, by the inlet system and, on the other hand, by an additional detector, wherein the drift tubes have opposite polarities. In this way, positive and negative ions can each be simultaneously measured in a corresponding drift tube.

Advantageously, the drift tube is constructed of alternatingly arranged metal rings and isolator rings, wherein each metal ring forms a corresponding DC voltage electrode around the drift space, or the drift tube is made of one or several tubes having low electrical conductivity.

Advantageously, the drift tube may have several AC voltage electrodes made of thin wire grids and arranged around the drift space, wherein the AC voltage electrodes are distributed along the length of the drift space and extend transversely through the drift space. Alternatively, the drift tube may advantageously have at least one auxiliary electrode arranged in the drift space, wherein an additional compensation voltage may be produced with his auxiliary electrode which affects the drift velocities of the ionized molecules in different ways.

In a particularly advantageous embodiment, an additional drift tube is delimited, on one hand, but the inlet system and, on the other hand, by an additional detector, wherein the drift tubes have opposite polarities. In this way, positive and negative ions can each be measured simultaneously in a corresponding drift tube.

The novel method for identification of gases and the corresponding device may be implemented in different ways. The will now be described with reference to an exemplary embodiment.

Figure 2:
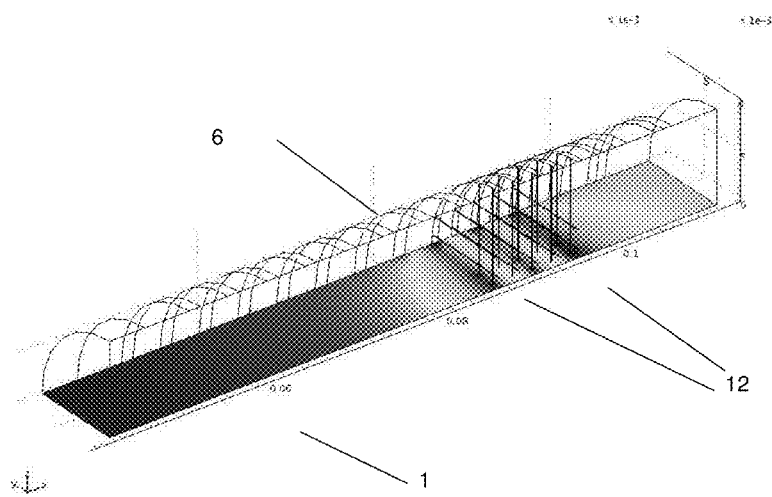
Figure 3:
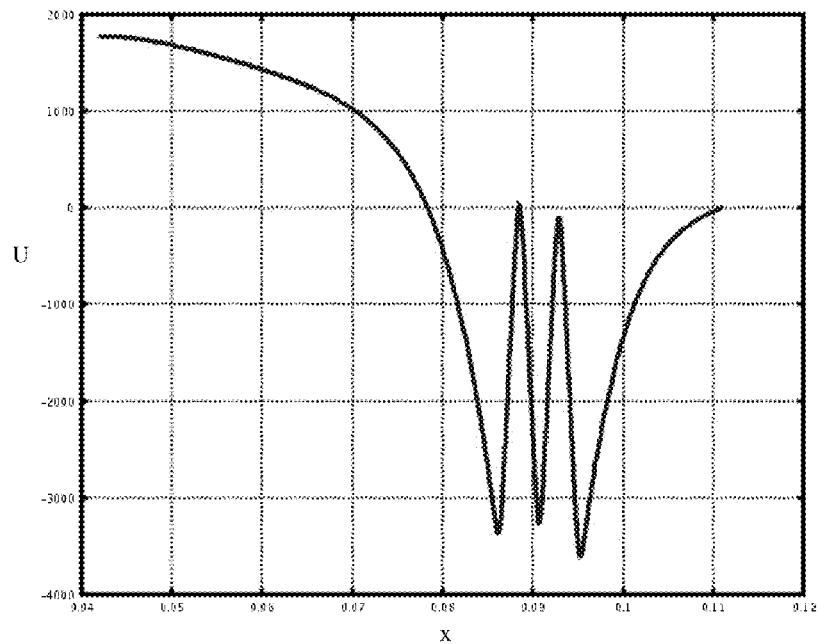
Figure 4:
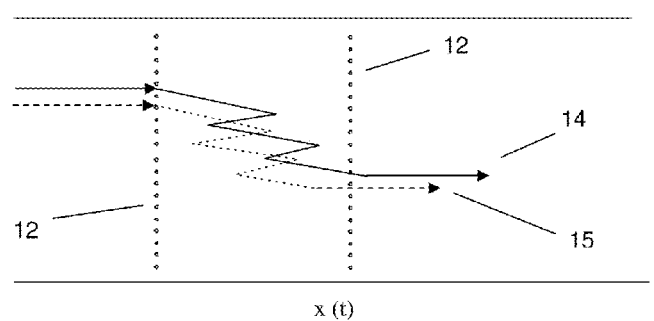
Figure 5:
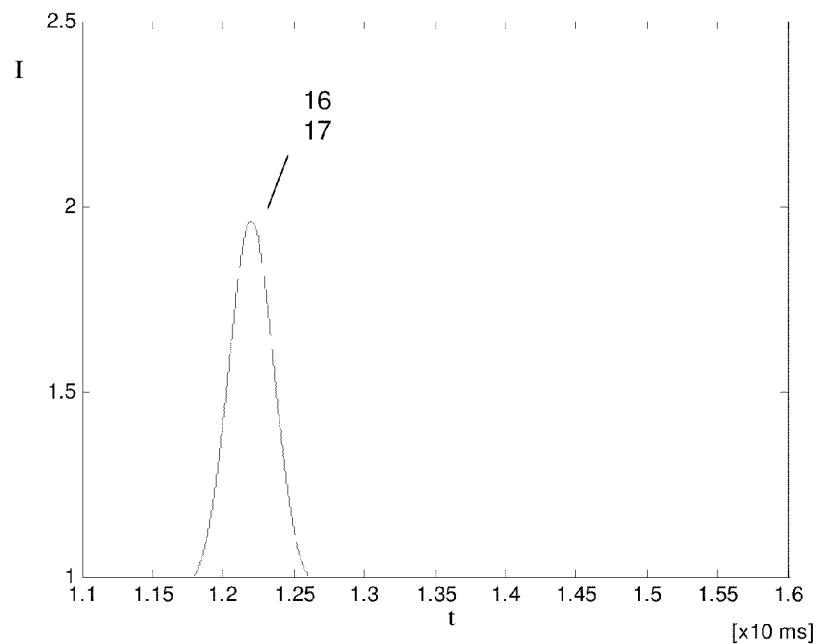
Figure 6:
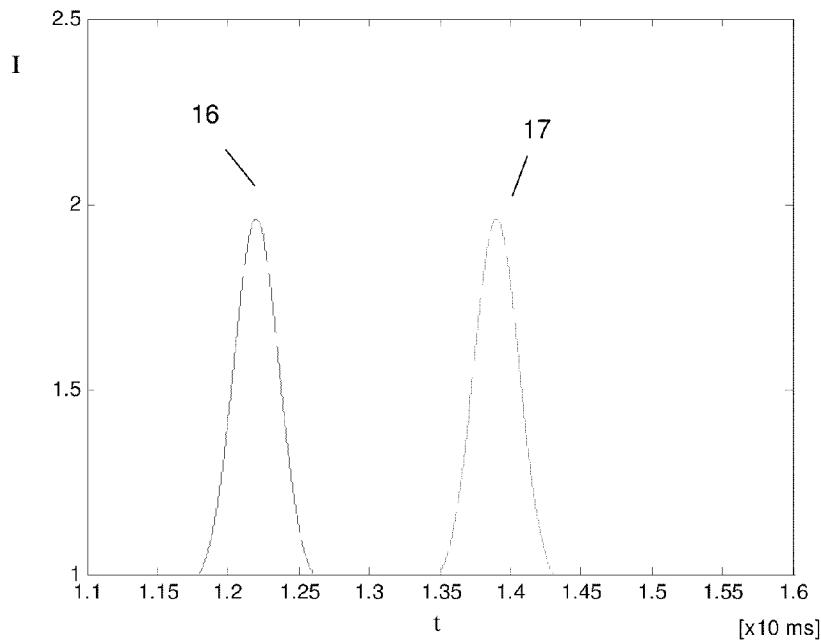
Figure 7:
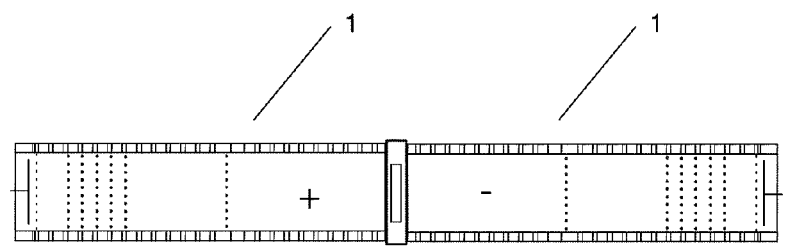
Figure 8:
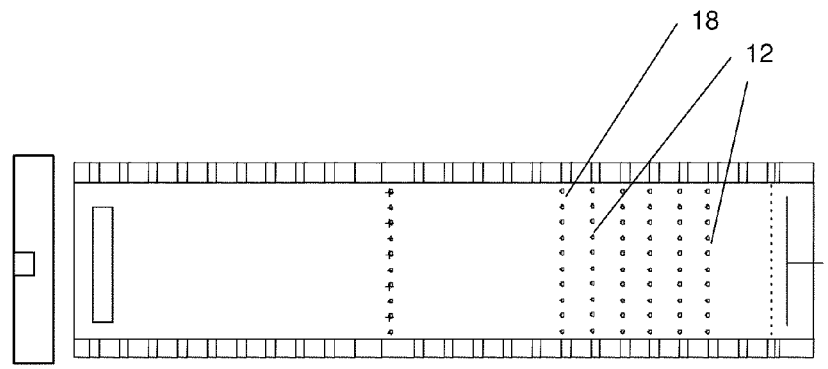

It is shown in:

FIG. 1 a schematic diagram of a drift tube,

FIG. 2 an exemplary potential distribution of the drift tube in a longitudinal cross-section, FIG. 3 an exemplary potential distribution in the drift tube at a fixed time, FIG. 4 an exemplary trajectory of ions in the drift tube, FIG. 5 an exemplary spectrum without an AC voltage, FIG. 6 an exemplary spectrum with an AC voltage, FIG. 7 a schematic diagram of two drift tubes, and FIG. 8 a schematic diagram of the drift tube with an auxiliary electrode.

According to an exemplary embodiment illustrated in FIG. 1, the novel device for identifying gases includes a drift tube 1 which is delimited, on one hand, by an inlet system 2 and, on the other hand, by a detector 3 made of a flat conductive disc.

An electrical opening and closing grid 4 is located in the drift tube 1, dividing the interior space of the drift tube 1 into a reaction space 5 and a drift space 6. The reaction space 5 is delimited by the inlet system 2, whereas the drift space 6 is delimited by the detector 3. In addition, an ion source 7 is arranged in the reaction space 5 proximate to the inlet system 2, and a shield grid 8 is arranged in the drift space 6 in front of the detector 3, wherein the ion source 7 has a radioactive $Ni^{63}$ foil and the shield grid 8 is provided for capacitive decoupling. The opening and closing grid 4 is a so-called Bradbury-Nielsen grid and includes two electrically conducting metal combs 13 which are arranged in a plane extending transversely through the drift tube 1, wherein the metal combs 13 are somewhat offset from one another with making contact with each other.

The drift tube 1 is constructed of alternatingly arranged metal rings 9 and insulator rings 10, wherein the metal rings 9 are electrically connected to one another with resistors and are hence implemented as DC voltage electrodes 11. The voltages applied to the DC voltage electrodes 11 are selected to produce constant field strengths in the reaction space 5 and in the drift space 6, respectively. In addition, the drift tube 1 has several AC voltage electrodes 12 made of thin metal wires and arranged around the drift space 6 and distributed along the length of the drift space 6 and extending transversely through the drift space 6.

During operation of the novel device for identifying gases according to the first exemplary embodiment, the chemical compound to be tested, including the ambient air, is introduced through the inlet system 2 into the ion source 7. The inlet system 2 may include a small opening or, for mobile systems, a silicone membrane.

The radiation from the $Ni^{63}$ foil in the ion source 7 ionizes predominantly air molecules from the ambient air. So-called reactant ions with water molecules are formed by subsequent reactions and depositions. These reactant ions subsequently form product ions via proton or proton abstraction reactions, which ionize the molecules of the tested chemical compound. These product ions travel in an electric field produced by the DC voltage electrodes 11 from the reaction space 5 to the opening and closing grid 4. The opening and closing grid 4 has two switching states. In the first switching state, the opening and closing grid 4 is closed. The metal combs 13 of the opening and closing grid 4 are at different potentials, wherein the potential difference between the metal combs 13 is about 100V. This potential difference generates a high field strength, which prevents ions from passing through. Ions from the reaction space 5 can hence not enter the drift space 6. In the second switching state, the opening and closing grid 4 is open. The potential difference between the metal combs 13 is then reduced within several microseconds, so that the opening and closing grid 4 temporarily allows ions to pass through and enter the drift space 6 from the reaction space 5.

This opening and closing grid 4, which is normally closed, is briefly opened at defined time intervals by temporarily reducing the potential difference between the metal combs 13. In the open state of the opening and closing grid 4, the ions are pulled by the electric field of the DC electrodes 11 from the reaction space 5 into the drift space 6 in the direction of the detector 3. On the way to the detector 3, the ions must pass through the electric field of the DC voltage electrodes 11 and the AC voltage electrodes 12, wherein these electric fields exert the same full pulling force on all ions having the same charge. However, because the ions continuously collide with the neutral air molecules, the velocity of the ions in the electric fields depends on the ion mass, for example the ion size and the ion shape.

The DC voltage electrodes 11 produce an electric field with a low field strength, which accelerates ions having identical diameters and shapes to identical drift velocities, whereas the ions having different diameters and shapes are accelerated to different drift velocities. In a region of the drift space 6, an asymmetric AC field of high field strength operating along the same coordinate axis is superimposed on the electric field of small field strength produced by the DC voltage electrodes 11, so that an additional force is applied to the ions between the AC voltage electrodes 12. The ions are then additionally decelerated or accelerated, so that the ions perform oscillatory movements between the AC voltage electrodes 12.

The ions therefore perform a constant basic movement in the drift space, on which the oscillatory movements between the AC voltage electrodes 12 are superimposed, so that the ions having different $\alpha(E)$-values are separated by the oscillatory movements. The $\alpha(E)$-values describe the non-linear dependence of the acceleration direction of the electric field, which is different for different chemical compounds. For example, the $\alpha(E)$-value may gradually increase with increasing field strength, may decrease with increasing field strength, or may first increase with increasing field strength and then again decrease at higher field strength. Accordingly, chemical compounds can be grouped into three categories, depending on the dependence on the field strength, wherein for ions of type A the mobility of the ions increases with increasing field strength, for ions of type C the mobility of the ions decreases with increasing field strength, and for ions of type B the mobility first increases with increasing field strength and then again decreases at higher field strengths. The ions, e.g., ions of type A and type C, are separated in the drift space 6 due to the different movements of the ions of type A and type C, with the movements composed of a constant basic movement and an oscillatory movement, because the ions of type A are additionally accelerated and the ions of type C are additionally decelerated in the asymmetric AC field.

The ions impact on the detector 3 at the end of the drift space 6. The detector is a Faraday collector, wherein the shield grid 8 arranged in front of the detector 3 is provided for capacitive decoupling between the ions in front of the detector 3 and the detector 3.

The measurement signals of the detector 3 are evaluated with a evaluation unit which is not illustrated in FIG. 1, wherein the drift times of the ionized molecules through a drift space 6 are determined from the opening times of the opening and closing grid 4 and the time of impact of the ions on the detector 3. The measured drift times are evaluated by comparing the measured drift times with the previously determined drift times of known chemical compounds, wherein the ionized molecules and therefore also the chemical compounds are identical for identical drift times.

FIG. 2 shows the potential curve at a fixed time for the drift tube 1 according to FIG. 1. It is evident that the electric potential increases significantly at the location of the AC voltage electrode 12 and steadily decreases outside the AC voltage electrodes 12. This suggests that the AC voltage electrodes 12, in the illustrated example, cannot be positioned at an arbitrary location in the drift tube 1, because for example at inadequately low potentials, which exist at the beginning of the drift space 6, the electric field strengths of the AC fields are too high, preventing ions from reaching the detector.

FIG. 3 shows an exemplary potential curve for the drift tube 1 according to FIG. 1, wherein the potential is referenced to the traveled distance x of the ions in the drift space 6 at a fixed point in time. As can be seen, the AC field, with reference to the drift tube 1 illustrated in FIG. 1 having five AC voltage electrodes 12, is applied to the first, the third and the fifth AC voltage electrode, whereas the second and fourth AC voltage electrode are at DC potential.

FIG. 4 shows exemplary trajectories of the ions in the drift space 6 between two adjacent AC voltage electrodes 12 of the drift tube 1, wherein the traveled distance x of the ions in the drift space 6 is with reference to the time t. The trajectory 14 shows ions with a high $\alpha(E)$ value, the trajectory 15 ions with a low $\alpha(E)$ value. Two trajectories of ions having the same mobility at a low field strength, i.e., identical mobility $K(E_{low})$, but different mobilities at high field strength $K(E_{high})$. Although no deflection occurs perpendicular to the field lines, it is illustrated in the diagram only to elucidate the particulars.

As seen in FIG. 4, ions which are not separated in the region before the AC voltage electrodes 12, which deflect the ions essentially only in the direction of the trajectory of the ions, travel different distances due to the effect of the high asymmetric AC voltages in the region of the AC voltage electrodes 12, thereby allowing separation. This also shows that the ions with different $\alpha(E)$ value have different mobilities at a high electric field strength, although they have the same mobilities at a low electric field strength, so that these ions have also different times of flight through the drift space 6 when the high asymmetric AC voltage is switched in, and reach the detector 3 at different times.

The drift velocities of the ions can be determined from the measured times of flight of the ions through the drift space or from the drift time at the maximum of the bell curve and the known length of the drift section. Because the time-of-flight is several milliseconds, spectra averaged over several measurements are displayed every second in form of a Gaussian bell curve. Exemplary signals measured at the detector 3 are shown in FIG. 5 and FIG. 6. FIG. 5 and FIG. 6 show exemplary spectra measured with the detector 3, wherein FIG. 5 shows an exemplary spectrum with a low DC voltage applied to the AC voltage electrodes 12, corresponding to the respective DC voltage potential, whereas FIG. 6 shows an exemplary spectrum when asymmetric AC voltages with high field strength are applied to the AC voltage electrodes 12.

FIG. 5 shows the times of flight 16, 17 of ions having the same mobility in a constant electric field with low field strength in the drift space 6 of the drift tube 1. These distributions of the times of flight are located on top of one another, so that ionized molecules of chemical compounds having an identical mobility at a low field strength $K(E_{low})$ cannot be separated from one another.

FIG. 6 shows the distributions 16, 17 of ions having identical mobility at low field strength under the influence of an alternating electric field in an asymmetric AC field of high field strength in the drift space 6 of the drift tube 1. These distributions of the times of flight 16, 17 are now clearly located next to each other, so that ionized molecules of chemical compounds having an identical mobility at a low field strength can now be separated from one another.

By changing the polarity of the electrodes 11, positive ions can be registered with the drift tube 1 at the detector 3 in a positive operating mode, and negative ions can be registered in a negative operating mode.

It would also be feasible to measure positive and negative ions by sequentially changing the polarity of the electric field in short time intervals. The DC voltage is applied to the electrodes 11 would then change polarity at certain time intervals, thereby also reversing the direction of the electric field between the electrodes.

A combination of two drift tubes 1 according to FIG. 7 would also be feasible, wherein the electric fields between the electrodes 11 of the first drift tube 1 have the opposite direction of the electric fields between the electrodes 11 of the second drift tube 1. With this combination of two drift tubes 1 with opposite polarity, positive and negative ions can be measured simultaneously in one corresponding drift tube 1.

In a particularly advantageous embodiment, the amplitude of the AC voltage may be changed. The drift times then also change, wherein these changes in the drift times can be used as an additional feature for identifying the tested chemical compound. The measured drift times can be evaluated by comparing the measured drift times with previously determined drift times of known chemical substances and compounds, which were obtained with and without changing the amplitude of the AC voltage.

Alternatively, instead of the drift tube 1 illustrated in FIG. 1 having five AC voltage electrodes 12, the number of AC voltage electrodes 12 and/or the applied AC voltage can also be changed.

It would also be feasible to construct the circular cylindrical drift tube not from alternating metal and isolator rings, as described above, but instead from a homogeneous material having low electrical conductivity. Conductive glasses, ceramics or plastics may be used, but also electrically insulating structures, which are coated with electrically conducting surfaces.

Alternatively, according to FIG. 8, an auxiliary electrode 18 could be arranged in the drift space 6 of the drift tube 1 for generating an additional compensation voltage. This produces an additional change in the drift time of the ionized molecules, which can be used as an additional feature for identifying of the tested chemical substance or compound.

The conversion processes occurring in the ion source 7 may also be replaced by others suitable processes. For example, the ions may be generated, instead of by radioactive radiation, for example by photo ionization or by corona discharge.

Because the start pulse of the opening and closing grid 4 is very short compared to the drift time of the ions and therefore a large portion of the ions is not used because these ionized molecules are neutralized on the closed grid, conventional methods can alternatively be used for optimizing the yield and therefore the detection limit, for example by increasing the ion throughput of the opening and closing grid 4. For example, the ion beam could be modulated with the switching times of the opening and closing grid 4 by using a mathematical transformation, for example a Hadamard- or Fourier-transformation, whereby the time-of-flight spectrum is computed from the signals measured at the detector 3.

Alternatively, the selectivity of the drift tube 1 could be optimized by using an additional reaction gas, for example a dopant gas. Chemical reactions, which are controlled for example by proton affinities for positive ions or electronegativities for negative ions, may be influenced with this reaction gas, thereby affecting the selectivity of the method. The selectivity of the drift to 1 may additionally be influenced by accumulation and deposition processes of the reaction gases or other electrically neutral gases on the ions at high field strengths.

In addition, combinations of the drift tube 1 with other sensors or detectors and/or with additional methods for increasing the selectivity, for example with an upstream gas chromatograph, are also contemplated.

LIST OF REFERENCES SYMBOLS

1 Drift tube
2 Inlet system
3 Detector
4 Opening and closing grid
5 Reaction space
6 Drift space
7 Ion source
8 Shield grid
9 Metal ring
10 Isolator ring
11 Electrode
12 AC field electrode
13 Metal comb
14 Trajectory
15 Trajectory
16 Distribution of times of flight
17 Distribution of times of flight
18 Auxiliary electrode

The invention claimed is:

1. A device for identification of gases, comprising an inlet system and at least one detector, wherein at least one drift tube is delimited, on one hand, by the inlet system and, on the other hand, by the at least one detector, and that in each drift tube an opening and closing grid is disposed which divides an interior space of the drift tube into a reaction space and a drift space, wherein an ion source is arranged in the reaction space and a shield grid is arranged in the drift space, wherein the drift tube comprises several DC voltage electrodes, arranged around and along the reaction space and the drift space, that produce a constant electric field in the reaction space and the drift space, and AC voltage electrodes, wherein the AC voltage electrodes are distributed regionally along the length of the drift space, wherein the AC voltage electrodes of the drift tube comprise at least three AC voltage electrodes in the drift space, that produce an alternating asymmetric electric field in a region of the drift space operating along the same coordinate axis as the constant electric field, and the DC voltage electrodes and the AC voltage electrodes are arranged around the drift space, that each ionized molecule in the region of the drift space has a drift velocity caused by a resulting electric field, wherein the resulting electric field is the constant DC voltage field, on which the asymmetric AC voltage field is locally superimposed, wherein change in the drift velocity is due to each ionized molecule performing, due to the resulting electric field, a constant drift movement on which an oscillatory movement is superimposed, so that the ionized molecule performs a drift movement in one direction, that runs parallel to field lines of the resulting electric field, with the oscillatory movement superimposed collinear thereto.

2. The device according to claim 1, wherein an additional drift tube is delimited, on one hand, by the inlet system and, on the other hand, by an additional detector, wherein the drift tubes have opposite polarities.

3. The device according to claim 1, wherein the drift tube comprises alternatingly arranged metal rings and isolator rings, wherein each metal ring is electrically connected around the drift space and forms a respective DC voltage electrode.

4. The device according to claim 1, wherein the drift tube comprises one or more tubes with low electric conductivity.

5. The device according to claim 1, wherein the AC voltage electrodes comprise thin wire grids extending transversely through the drift space.

6. The device according to claim 1, wherein the opening and closing grid comprises two electrically conducting metal combs, which are arranged in a plane extending transversely through the drift tube, wherein the metal combs are slightly offset from one another and do not contact each other.

7. The device according to claim 6, wherein the opening and closing grid has two switching states, wherein:
in a first switching state, the opening and closing grid is closed, because the metal combs are at different potentials and this potential difference produces a high field strength, thereby preventing ions from passing through the opening and closing grid, and
in a second switching state, the opening and closing grid is open, because the metal combs are at the same potential, so that no electric field at all or only an electric field with a low field strength is produced, allowing ions to pass through the opening and closing grid.

8. The device according to claim 1, wherein the shield grid is arranged in front of the detector, wherein the shield grid provides capacitive decoupling.

9. The device according to claim 1, wherein the drift tube comprises at least one auxiliary electrode which is arranged in the drift space for generating an additional compensation voltage.

10. The device according to claim 1, wherein the drift tube is constructed as a circular cylinder.

11. A method for identification of gases, wherein the gases to be identified are ionized and drift times of the ionized molecules through a drift space are measured and the measured drift times are evaluated by a gas identification device comprising at least one drift tube an inlet system and at least one detector, wherein the at least one drift tube is delimited, at a first end end, by the inlet system and, at a second end, by the at least one detector, wherein an opening and closing grid is disposed within the at least one drift tube and divides an interior of the drift tube into a reaction space and the drift space, wherein the drift tube comprises several DC voltage electrodes, arranged around and along the reaction space and drift space, that produce a constant electric field in the reaction space and drift space, and AC voltage electrodes, wherein the AC voltage electrodes are distributed regionally along the length of the drift space, that produce an alternating asymmetric electric field in a region of the drift space operating along the same coordinate axis as the constant electric field, wherein the DC voltage electrodes and the AC voltage electrodes are arranged around the drift space, wherein, for measurement of the drift times, the ionized molecules are firstly accelerated to a drift velocity in the drift space by the constant electric field and secondly ionized molecules that have the same drift velocity commonly enter the region in the drift space, wherein a resulting electric field formed by the constant electric field, on which the alternating asymmetric electric field is locally superimposed, additionally accelerates or decelerates the ionized molecules so that each ionized molecule has a drift velocity caused by the resulting electric field, wherein change in the drift velocity is due to each ionized molecule performing, due to the resulting electric field, a constant drift movement on which an oscillatory movement is superimposed, so that the ionized molecules perform a drift movement in one direction, that runs parallel to field lines of the resulting electric field, with the oscillatory movement superimposed collinear thereto.

12. The method according to claim 11, wherein positive and/or negative ions are used as ionized molecules.

13. The method according to claim 11, wherein each ionized molecule is accelerated and decelerated several times, wherein on average, depending on the material properties of the molecule, the acceleration is greater or smaller than the deceleration.

14. The method according to claim 11, wherein the DC voltage field has a low electric field strength, and the asymmetric AC voltage field has a high electric field strength.

15. The method according to claim 14, wherein an amplitude of asymmetric AC voltage is changed during the measurement of the drift times.

16. The method according to claim 11, wherein, for identification of the chemical compounds, the measured drift times are compared with previously determined drift times of known chemical compounds.

17. The method according to claim 16, wherein the comparison between the measured drift times and the known drift times of chemical compounds is performed using mathematical or statistical methods.

18. The method according to claim 11, wherein the drift times of ionized molecules having identical mobilities at low electric field strengths are compared with the drift times of these ionized molecules after the asymmetric AC voltage field with a high electric field strength generated by the AC voltage electrodes is switched in, and that for identification of the chemical compounds, the measured drift times are compared with the previously determined drift times.

* * * * *